United States Patent
Ting et al.

(10) Patent No.: US 8,469,895 B2
(45) Date of Patent: Jun. 25, 2013

(54) DERIVING CENTRAL AORTIC SYSTOLIC PRESSURE AND ANALYZING ARTERIAL WAVEFORM DATA TO DERIVE CENTRAL AORTIC SYSTOLIC PRESSURE VALUES

(75) Inventors: Choon Meng Ting, Singapore (SG); Ngak Hwee Chua, Singapore (SG)

(73) Assignee: Healthstats International Pte Ltd, Singapore (SG)

( * ) Notice: Subject to any disclaimer, the term of this patent is extended or adjusted under 35 U.S.C. 154(b) by 1646 days.

(21) Appl. No.: 11/859,922

(22) Filed: Sep. 24, 2007

(65) Prior Publication Data

US 2008/0306393 A1  Dec. 11, 2008

Related U.S. Application Data

(60) Provisional application No. 60/942,642, filed on Jun. 7, 2007.

(51) Int. Cl.
*A61B 5/02* (2006.01)
(52) U.S. Cl.
USPC .......................... 600/485; 600/490; 600/503
(58) Field of Classification Search
USPC .................. 600/480–481, 490, 503
See application file for complete search history.

(56) References Cited

U.S. PATENT DOCUMENTS

| 6,428,482 B1 | 8/2002 | Sunagawa et al. |
| 6,443,906 B1 * | 9/2002 | Ting et al. ................ 600/490 |
| 2003/0236465 A1 | 12/2003 | Narimatsu et al. |
| 2007/0185400 A1 | 8/2007 | O'Rourke |

FOREIGN PATENT DOCUMENTS

WO  2006072776 A1  7/2006

OTHER PUBLICATIONS

International Search Report received in PCT/SG2007/000161 dated Aug. 23, 2007.

* cited by examiner

*Primary Examiner* — Patricia Mallari
*Assistant Examiner* — Vasuda Ramachandran
(74) *Attorney, Agent, or Firm* — Edell, Shapiro & Finnan, LLC

(57) ABSTRACT

A method of deriving central aortic systolic pressure comprises (a) creating a set having a predetermined number of blood pressure measurements, the set representative of an arterial waveform; (b) determining an integer interval value; (c) averaging a series of consecutive blood pressure measurement readings in the set equal to the integer interval value commencing from the $f^{th}$ blood pressure measurement in the set; (d) storing the averaged value in a central aortic systolic pressure set; and (e) setting the central aortic systolic pressure as the highest value in the central aortic pressure set. Steps (c) and (d) are repeated with the value of f being incremented by 1 each time until the value of f plus the integer interval value equals the predetermined number of blood pressure measurements in the set.

16 Claims, 3 Drawing Sheets

DERIVING CENTRAL AORTIC SYSTOLIC PRESSURE AND ANALYZING ARTERIAL WAVEFORM DATA TO DERIVE CENTRAL AORTIC SYSTOLIC PRESSURE VALUES

CROSS REFERENCE TO RELATED APPLICATION

This application claims priority from U.S. Provisional Patent Application Ser. No. 60/942,642, entitled "Method of Deriving Central Aortic Systolic Pressure and a Method of Analyzing Arterial Waveform Data to Derive Central Aortic Systolic Pressure Values", and filed Jun. 7, 2007, the disclosure of which is incorporated herein by reference in its entirety.

FIELD

A method of deriving the central aortic systolic pressure and a method of analyzing arterial waveform data to derive central aortic systolic pressure values are described herein.

BACKGROUND

The following discussion of this background section is intended to facilitate an understanding of the present invention. However, it should be appreciated that the discussion is not an acknowledgment or admission that any of the material referred to was published, known or part of the common general knowledge in any jurisdiction as at the priority date of the application.

Heart disease is a serious health problem in developed countries. One indicator of potential heart disease is variances in the blood pressure of the living body from a designated range of "normal" values.

A common method of determining the blood pressure of a living body is to take a brachial blood pressure reading (both systolic and diastolic) of the living body using a pressure cuff. These values are commonly then used as surrogate central aortic pressure values. While this assumption has historically been proven as beneficial in indicating potential heart disease, recent studies have shown that a "normal" brachial blood pressure value measured in this manner may mask abnormal central aortic systolic pressure values.

One solution to this problem has been adopted by Atcor Medical Pty Ltd of West Ryde, New South Wales, Australia. Atcor's solution uses a proprietary transfer formula to convert a radial pressure waveform to a central aortic blood pressure waveform. However, this formula is only available through proprietary software made commercially available by Atcor for use with its SphygmoCor™ blood pressure monitoring system. More importantly, the formula is based on a correlation value determined through testing on a cross-representation of patients and therefore may introduce error in central aortic pressure readings on patients that fall outside the realms of the cross-representative sample.

SUMMARY OF THE INVENTION

Throughout this document, unless otherwise indicated to the contrary, the terms "comprising", "consisting of", and the like, are to be construed as non-exhaustive, or in other words, as meaning "including, but not limited to".

In the context of the present description of the embodiments of the invention, the term "living body" is a reference to the body at the time of generation of the arterial waveform. The invention is not to be considered as limited to exclude the calculation of a central aortic pressure value from an arterial waveform of a since deceased patient.

In accordance with the invention, a first method of deriving the central aortic systolic pressure and a second method of analyzing arterial waveform data to derive central aortic systolic pressure values are described herein. In accordance with the first method of the invention, the invention is particularly suited to deriving the central aortic systolic pressure from an arterial waveform. However, in accordance with the second method of the invention, the invention is suited towards analyzing an arterial waveform dataset to derive a corresponding central aortic systolic pressure dataset.

In accordance with a first aspect of the invention there is a method of deriving central aortic systolic pressure comprising the steps of:

a) creating a set having a predetermined number of blood pressure measurements, the set representative of an arterial waveform;

b) determining an integer interval value;

c) averaging a series of consecutive blood pressure measurement readings in the set equal to the integer interval value commencing from the $f^{th}$ blood pressure measurement in the set;

d) storing the averaged value in a central aortic systolic pressure set; and e) setting the central aortic systolic pressure as the highest value in the central aortic pressure set, where steps c. and d. are repeated with the value of f commencing at 1 and being incremented by 1 each time until the value of f plus the integer interval value equals the predetermined number of blood pressure measurements in the set.

The set of blood pressure measurements should substantially equate to a uniform distribution of values from the arterial waveform. In particular, the method preferably includes the step of determining the duration of the arterial waveform. The duration of the wave form can then be used to determine the predetermined number according to the following formula:

$$\text{Predetermined number} = sr \times t$$

where
  sr=the sample rate, in Hz, of a measuring device used to record the blood pressure measurements in the set; and
  t=the duration of the arterial waveform The integer interval value may be division of the sample rate. Ideally, however, the integer interval value is the sample rate divided by 4.

Alternatively, the integer interval value may be a division of the predetermined number of blood pressure measurements in the set of blood pressure measurements. Ideally, using this technique, the integer interval value may fall within a range the boundaries of which are determined as follows:

$$i_{range} = n/(t \times v) \pm (n/(t \times 30))$$

where
  n is the predetermined number of blood pressure measurements in the set;
  t is the duration of the waveform (in seconds); and
  v is a predetermined division value.

It is preferred, but not essential, that in calculating the above range, the value of v be set to 4.

In one alternative configuration, the integer interval value is equal to 60 divided by a predetermined division value. In another alternative configuration, the integer interval value is 15.

The predetermined number of blood pressure measurements in the set is equal to or greater than 15. However, it is preferred that the predetermined number of blood pressure measurements in the set is at least 30.

In its most preferred arrangement the predetermined number of blood pressure measurements in the set is at least 30 and the interval is 15.

In accordance with a second aspect of the invention there is a method of analyzing arterial waveform data to derive central aortic systolic pressure values comprising the steps of:
 a. receiving an arterial waveform dataset
 b. dividing each arterial waveform in the arterial waveform dataset into a representative set of blood pressure measurements having a predetermined number;
 c. determining an integer interval value for the set being processed;
 d. averaging a series of consecutive blood pressure measurement readings in the set equal to the integer interval value commencing from the f$^{th}$ blood pressure measurement in the set;
 e. storing the averaged value in a central aortic systolic pressure set; and
 f. storing the highest value in the central aortic pressure set in a central aortic systolic pressure value set at a position corresponding to the position the arterial waveform being processed occupies in the arterial waveform dataset, where steps b. through f. are repeated for each arterial waveform in the arterial waveform dataset and, for each such repetition, steps d. and e. are further repeated with the value of f commencing at 1 and being incremented by 1 each time until the value of f plus the integer interval value equals the predetermined number of blood pressure measurements in the set being processed.

In accordance with a third aspect of the invention there is a method of analyzing arterial waveform data to derive central aortic systolic pressure values comprising the steps of:
 a. receiving an arterial waveform dataset, where each arterial waveform in the dataset comprises a representative set of blood pressure measurements having a predetermined number;
 b. determining an integer interval value for the set being processed;
 c. averaging a series of consecutive blood pressure measurement readings in the set equal to the integer interval value commencing from the f$^{th}$ blood pressure measurement in the set;
 d. storing the averaged value in a central aortic systolic pressure set; and
 e. storing the highest value in the central aortic pressure set in a central aortic systolic pressure value set at a position corresponding to the position the arterial waveform being processed occupies in the arterial waveform dataset, where steps b. through e. are repeated for each arterial waveform in the arterial waveform dataset and, for each such repetition, steps c. and d. are further repeated with the value of f commencing at 1 and being incremented by 1 each time until the value of f plus the integer interval value equals the predetermined number of blood pressure measurements in the set being processed.

The predetermined number of blood pressure measurements for at least one arterial waveform in the dataset may differ from the predetermined number of blood pressure measurements for the other arterial waveforms in the dataset.

In respect of both the second and third aspects of the invention, the set of blood pressure measurements should substantially equate to a uniform distribution of values from the arterial waveform.

Ideally, the method further includes the step of determining the duration of the arterial waveform. The duration of the wave form can then be used to determine the predetermined number according to the following formula:

$$\text{Predetermined number} = sr \times t$$

where
 sr = the sample rate, in Hz, of a measuring device used to record the blood pressure measurements in the set; and
 t = the duration of the arterial waveform The integer interval value may be a division of the sample rate (sr). Preferably, the integer interval value is the sample rate divided by 4.

Alternatively, the integer interval value may be a division of the predetermined number of blood pressure measurements in the set of blood pressure measurements. Ideally, using this technique, the integer interval value is within a range the boundaries of which are determined as follows:

$$i_{range} = n/(t \times v) \pm (n/t \times 30))$$

where
 n is the predetermined number of blood pressure measurements in the set;
 t = the duration of the waveform (in seconds); and
 v is a predetermined division value.

In this formula, it is further preferred that the value of v be set to 4.

In one alternative configuration, the integer interval value is equal to 60 divided by a predetermined division value. In another alternative configuration, the integer interval value is 15.

The predetermined number of blood pressure measurements in the set should be equal to or greater than 15. A set of 30 blood pressure measurements is preferred.

In accordance with a fourth aspect of the invention there is a system for deriving central aortic systolic pressure comprising:
 an arterial waveform measuring device; and
 a processing unit,
where, the arterial waveform measuring device takes a blood pressure measurement at predetermined intervals until at least one arterial waveform is represented by the set of blood pressure measurements taken, the set of blood pressure measurements representative of one arterial waveform then being communicated to the processing unit which:
 a) determines an integer interval value;
 b) averages a series of consecutive blood pressure measurement readings in the set equal to the integer interval value commencing from the f$^{th}$ blood pressure measurement in the set;
 c) stories the averaged value in a central aortic systolic pressure set; and
 d) sets the central aortic systolic pressure as the highest value in the central aortic pressure set,
wherein steps b. and c. are repeated with the value of f commencing at 1 and being incremented by 1 each time until the value of f plus the integer interval value equals the number of blood pressure measurements in the set.

In accordance with further aspects of the invention there are computer readable medium having software thereon to perform the methods described in the first, second and third aspects of the invention.

BRIEF DESCRIPTION OF THE DRAWINGS

The invention will now be described, by way of example only, with reference to the accompanying drawings, in which.

PREFERRED EMBODIMENTS OF THE INVENTION

Particular embodiments of the present invention will now be described with reference to the accompany drawings. The terminology used herein is for the purpose of describing particular embodiments only and is not intended to limit the scope of the present invention. Additionally, unless defined otherwise, all technical and scientific terms used herein have the same meanings as commonly understood by one or ordinary skill in the art to which this invention belongs.

In accordance with a first embodiment of the invention there is a method of determining central aortic pressure 10. The method 10 is illustrated in flow chart form in FIG. 1.

Figure 1:
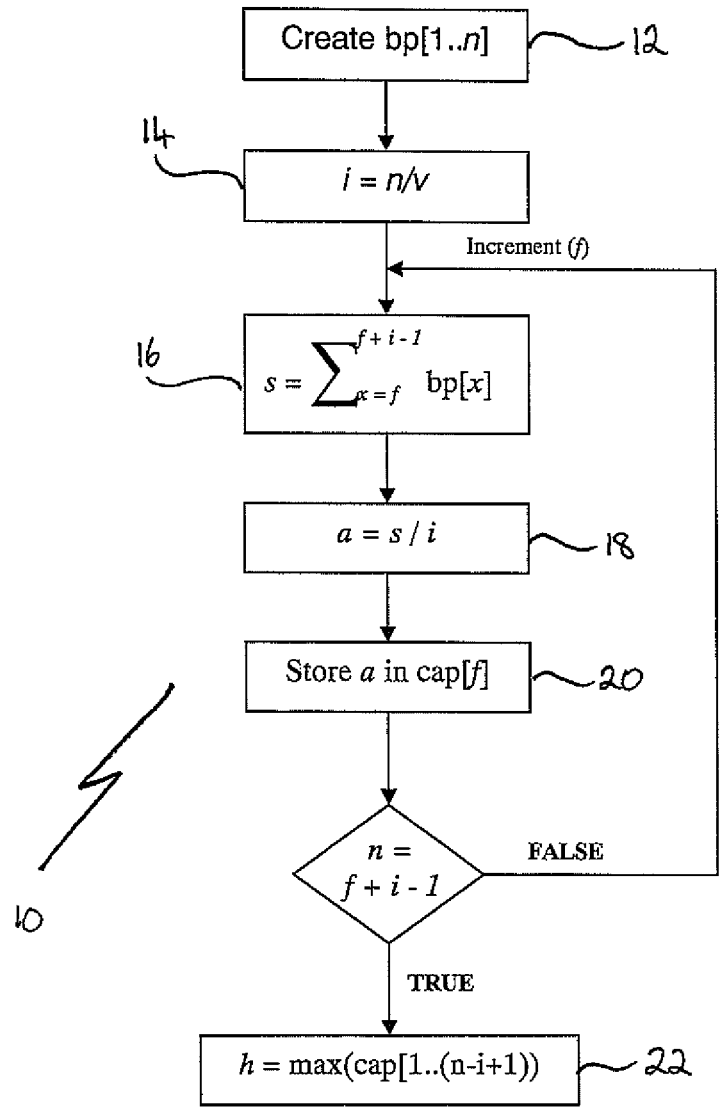
FIG. 1 is a flow chart of a method of determining the central aortic pressure of a living body in accordance with a first embodiment of the present invention.
Figure 2:
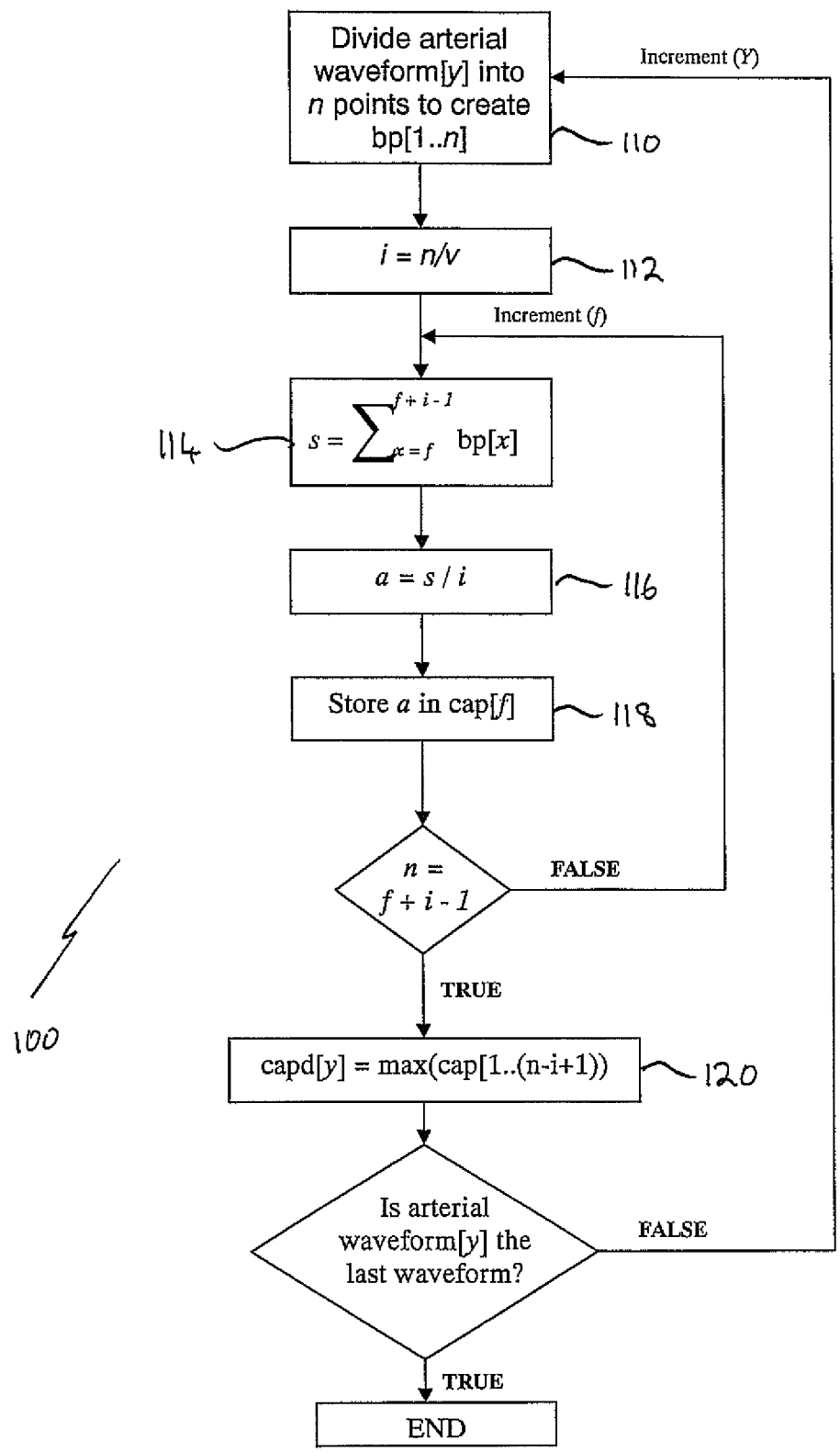
FIG. 2 is a flow chart of a method of analyzing an arterial waveform dataset to produce a corresponding central aortic pressure dataset in accordance with a second embodiment of the present invention.
Figure 3:
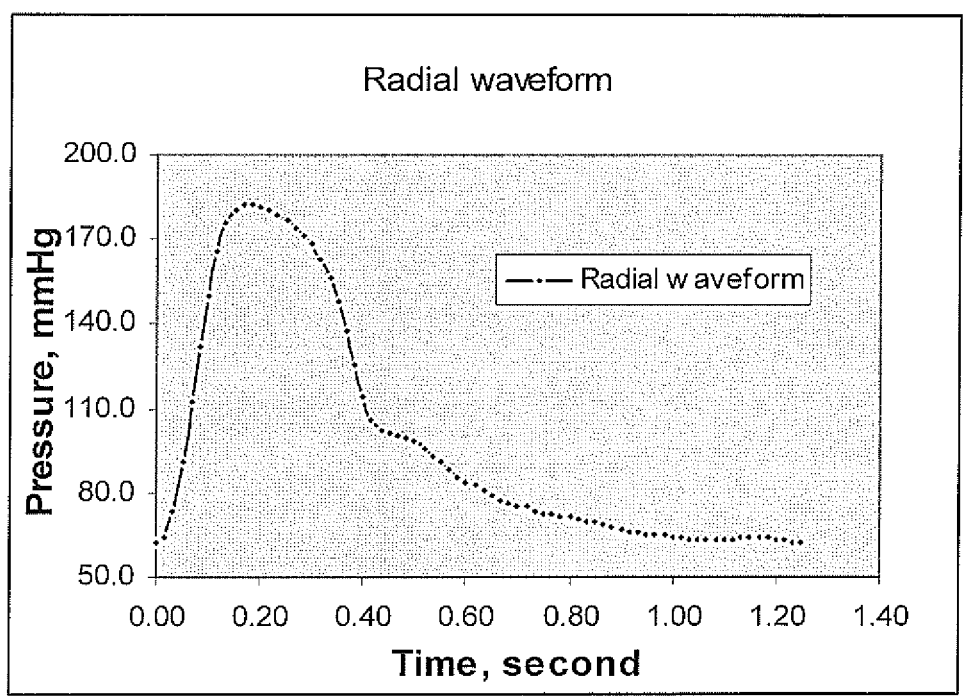
FIG. 3 is an illustrative arterial waveform that can be processed by any embodiment of the current invention to obtain a central aortic pressure value.

As shown in FIG. 1, the method 10 commences by the creation of a set of blood pressure measurements from a living body representative of an arterial waveform (step 12). The set of blood pressure measurements has a predetermined number of measurements (n). At step 14, the predetermined number n is divided by a preset value (v) to determine an integer interval value (i). In this manner, the integer interval value (i) may be subjected to an absolute or rounding mathematical function.

The following steps are then repeated, commencing with a first blood pressure measurement bp[(f)]:

The blood pressure measurements {bp[f], bp[f+1], bp[f+2], bp[f+3], . . . , bp[f+i−1]} are summed (step 16) to form a value s;

The summed value s be divided by the interval value i to form an average blood pressure value (a) (step 18).

The average blood pressure value a is stored in a central aortic pressure set of values (step 20).

The above steps (steps 16 to 20) are repeated until f+i−1 is equal to n.

Step 22 sees the central aortic pressure set of values analyzed to determine the highest value in the set (h). The highest value h is then used as a value substantially representative of the central aortic systolic pressure of the living body.

In accordance with a second embodiment of the present invention there is a method of analyzing an arterial waveform dataset to produce a corresponding central aortic pressure dataset 100. A common precursor to this embodiment is that a medical professional obtains an arterial waveform representation of the blood pressure of a living body according to any technique as would be known to the person skilled in the art. This arterial waveform representation is then provided to a central processing station for determination of the corresponding central aortic pressure. Following receipt of the arterial waveform representation the central processing station operates as follows:

For each arterial waveform in the waveform dataset, a corresponding central aortic pressure value a is determined and stored in the central aortic pressure dataset according to the following process.

The arterial waveform 102 being processed is divided into a set of representative blood pressure measurements (step 110). The set of blood pressure measurements has a predetermined number of measurements (n). At step 112, the predetermined number n is divided by a preset value (v) to determine an integer interval value (i).

The following steps are then repeated, commencing with a first blood pressure measurement bp[(f)]:

The blood pressure measurements {bp[f], bp[f+1], bp[f+2], bp[f+3], . . . , bp[f+i−1]} are summed (step 114) to form a value s;

The summed value s be divided by the interval value i to form an average blood pressure value (a) (step 116).

The average blood pressure value a is stored in a central aortic pressure set of values (step 118).

The above steps (steps 114 to 118) are repeated until f+i−1 is equal to n.

Step 120 sees the central aortic pressure set of values analyzed to determine the highest value in the set (h). The highest value h is then stored in the central aortic pressure dataset as the central aortic systolic pressure value corresponding with the arterial waveform processed.

The above steps are then repeated until such time as a corresponding central aortic pressure value has been calculated for each arterial waveform in the waveform dataset.

In accordance with a third embodiment of the invention, where like numerals reference like steps, there is a method of analyzing an arterial waveform dataset to produce a corresponding central aortic pressure dataset (not shown). This embodiment is based on experiments conducted by the applicant where it has been found that the n value can be any value in excess of 15.

In this embodiment, while it is preferred that the v value be 4 to determine an appropriate interval, a substantially accurate aortic pressure value has been able to be obtained where the interval value is in a range, the limits of which are determined as follows:

$$i_{range} = n/(t \times v) \pm (n/(t \times 30))$$

where in this embodiment, the variable t is representative of the duration of a single waveform (in seconds).

This embodiment will now be described in more detail in the context of the following example:

In accordance with step 12, a set of blood pressure measurements from a living body representative of an arterial waveform are created. The measurements are as follows (in order, from left to right, top to bottom):

| 62.0  | 63.6  | 73.1  | 91.1  | 112.3 | 132.1 | 149.6 | 165.4 | 176.0 | 180.7 |
| 182.0 | 181.9 | 181.3 | 180.2 | 178.8 | 176.8 | 174.4 | 171.5 | 167.9 | 163.1 |
| 156.4 | 147.8 | 137.1 | 125.1 | 114.0 | 106.2 | 102.3 | 101.1 | 100.7 | 99.8  |
| 98.2  | 95.9  | 93.2  | 90.6  | 88.1  | 85.8  | 83.9  | 82.2  | 80.4  | 78.7  |
| 77.2  | 76.2  | 75.5  | 74.7  | 73.7  | 72.7  | 72.0  | 71.5  | 71.1  | 70.5  |
| 69.9  | 69.1  | 68.4  | 67.5  | 66.9  | 66.1  | 65.5  | 65.1  | 64.9  | 64.8  |
| 64.4  | 63.8  | 63.3  | 62.9  | 62.7  | 62.8  | 63.1  | 63.3  | 63.5  | 63.6  |
| 63.6  | 63.5  | 63.4  | 63.0  | 62.5  | 62.0  |       |       |       |       |

The time duration taken to complete this waveform is 1.27 seconds.

This sets the n value at 76. With a v value of 4, the interval value range ($i_{range}$) is determined as follows:

$$i_{range} = n/(t \times v) \pm (n/(t \times 30)), \text{ therefore}$$

$$i_{range} = 76/(1.27 \times 4) \pm (76/(1.27 \times 30)), \text{ therefore}$$

$$i_{range} = 14.96 \pm (1.99)$$

As it is not possible for intervals to be anything other than integer values, the $i_{range}$ value is restricted to the range of 13 to 17. For the purposes of this example, an i value of 15 shall be used.

Following the requirements of steps 16 through 20, a central aortic pressure set of values is created having the following values:

| {140.7 | 148.3 | 155.7 | 162.3 | 167.4 | 170.8 |
|---|---|---|---|---|---|
| 172.4 | 172.3 | 170.4 | 167.0 | 162.5 | 157.5 |
| 152.2 | 146.8 | 141.5 | 136.3 | 131.0 | 125.8 |
| 120.6 | 115.4 | 110.4 | 105.7 | 101.5 | 97.8 |
| 94.8 | 92.5 | 90.5 | 88.8 | 87.1 | 85.4 |
| 83.6 | 81.9 | 80.3 | 78.9 | 77.6 | 76.4 |
| 75.3 | 74.4 | 73.4 | 72.6 | 71.8 | 71.1 |
| 70.3 | 69.6 | 69.0 | 68.4 | 67.8 | 67.3 |
| 66.7 | 66.2 | 65.7 | 65.2 | 64.8 | 64.5 |
| 64.2 | 64.0 | 63.8 | 63.7 | 63.6 | 64.5 |
| 63.3 | 63.1} | | | | |

As can be seen the central aortic pressure set of values has 62 elements to it, being the value equal to n−i+1. From this set, it is apparent that the highest value in the set (h) is in fact the seventh data element (172.4). Accordingly the central aortic systolic pressure of the living body is determined as 172.4.

In a fourth, and most preferred embodiment of the invention, there is a method of determining central aortic pressure as described in the first embodiment of the invention. However, in this embodiment, the predetermined number n is determined according to the following formula:

$$n = sr \times t$$

where
sr=the sample rate (in hertz) of a measuring device used to record the blood pressure measurements in the set bp; and
t=the time taken (in seconds) to complete one arterial waveform.

In this embodiment, the blood pressure measurements in the set bp are the measurement values taken by the measuring device at each repetition of the sample rate. Furthermore, in this embodiment of the invention, the interval value is in a range, the limits of which are determined as follows:

$$i_{range} = sr/v \pm (sr/30)$$

In this case, sr again represents the sample rate (in hertz) of a measuring device used to record the blood pressure measurements in the set bp. Additionally, the v value is preferably 4. This formula is only applicable though when the sr value is in excess of 30.

Using the same set of blood pressure measurements as set out above, but this time in a situation where the set is the culmination of blood pressure values taken by a sampling device having a sample rate (sr) of 60 measurements per second, the $i_{range}$ value is calculated as follows:

$$i_{range} = sr/v \pm (sr/30)$$

$$i_{range} = 60/4 \pm (60/30)$$

$$i_{range} = 15 \pm 2$$

This results in an $i_{range}$ value of between 13 and 17. The rest of the method can then proceed as set out in the first embodiment above.

It should be appreciated by the person skilled in the art that the above invention is not limited to the embodiments described. In particular, the following modifications and improvements may be made without departing from the scope of the present invention:

The set of blood pressure measurements may be obtained from a device that is also adapted to perform the method of the present invention. Alternatively, the set of blood pressure measurements may be obtained from a separate device and communicated to a further apparatus adapted to perform the method of the present invention.

The second embodiment of the invention may be modified such that the waveform dataset does not contain waveforms—in its place the waveform dataset data may contain sets of data representative of such waveforms. In this manner, the processing of step 110 may be omitted.

The waveform dataset may be supplied to the entity performing the method along with the duration of each waveform in the dataset. Alternatively, the entity performing the method may determine the duration of each waveform independently through alternate means (such as by receiving graphs having a fixed time value for predetermined lengths of the x axis and approximating the duration of the waveform based on this time/distance relationship or by deriving the duration from other composite values, such as the sample rate used to generate the set of blood pressure measurements).

To be the most representative of an arterial waveform, the blood pressure values that form the set bp should be of uniform distribution along the arterial waveform.

It should be further appreciated by the person skilled in the art that the features described above, where not mutually exclusive, can be combined to form yet further embodiments of the invention.

What is claimed:

1. A system for deriving central aortic systolic pressure comprising:
    an arterial waveform measuring device; and
    a processing unit;
    wherein the arterial waveform measuring device takes a set of blood pressure measurements at predetermined intervals until at least one arterial waveform is represented by the set of blood pressure measurements taken, the set of blood pressure measurements representative of one arterial waveform then being communicated to the processing unit which:
    a) determines an integer interval value;
    b) averaging a series of consecutive blood pressure measurement readings in the set equal to the integer interval value commencing from an $f^{th}$ blood pressure measurement in the set;
    c) stores the averaged value in a central aortic systolic pressure set; and
    d) sets the central aortic systolic pressure as the highest value in the central aortic pressure set;
    wherein steps (b) and (c) are repeated with the value of f commencing at 1 and being incremented by 1 each time until the value of f plus the integer interval value equals the number of blood pressure measurements in the set.

2. A computer readable medium that, in use, is non-transitory, the computer readable medium having embodied thereon software comprising computer code, the computer code comprising instructions to derive central aortic systolic pressure, the instructions comprising:
    (a) creating a set having a predetermined number of blood pressure measurements, the set representative of an arterial waveform;
    (b) determining an integer interval value;
    (c) averaging a series of consecutive blood pressure measurement readings in the set equal to the integer interval value commencing from an $f^{th}$ blood pressure measurement in the set;
    (d) storing the averaged value in a central aortic systolic pressure set; and (e) setting the central aortic systolic pressure as the highest value in the central aortic pressure set;

wherein a value of f corresponds with the $f^{th}$ blood pressure measurement, steps (c) and (d) are repeated with the value of f commencing at 1 and being incremented by 1 each time until the value of f plus the integer interval value equals the predetermined number of blood pressure measurements in the set.

3. A computer readable medium that, in use, is non-transitory, the computer readable medium having embodied thereon software comprising computer code, the computer code comprising instructions to analyze arterial waveform data to derive central aortic systolic pressure values, the instructions comprising:

(a) receiving an arterial waveform dataset;

dividing each arterial waveform in the arterial waveform dataset into a representative set of blood pressure measurements having a predetermined number;

(b) determining an integer interval value for the set being processed;

(c) averaging a series of consecutive blood pressure measurement readings in the set equal to the integer interval value commencing from an $f^{th}$ blood pressure measurement in the set;

(d) storing the averaged value in a central aortic systolic pressure set; and (e) storing the highest value in the central aortic pressure set in a central aortic systolic pressure value set at a position corresponding to the position the arterial waveform being processed occupies in the arterial waveform dataset;

wherein a value of f corresponds with the $f^{th}$ blood pressure measurement, the steps of (a)-(e) are repeated for each arterial waveform in the arterial waveform dataset and, for each such repetition, steps of (c) and (d) are further repeated with the value of f commencing at 1 and being incremented by 1 each time until the value of f plus the integer interval value equals the predetermined number of blood pressure measurements in the set being processed.

4. A computer readable medium that, in use, is non-transitory, the computer readable medium having embodied thereon software comprising computer code, the computer code comprising instructions to analyze arterial waveform data to derive central aortic systolic pressure values, the instructions comprising:

a) receiving an arterial waveform dataset, where each arterial waveform in the dataset comprises a representative set of blood pressure measurements having a predetermined number;

b) determining an integer interval value for the set being processed;

c) averaging a series of consecutive blood pressure measurement readings in the set equal to the integer interval value commencing from an $f^{th}$ blood pressure measurement in the set;

d) storing the averaged value in a central aortic systolic pressure set; and e) storing the highest value in the central aortic pressure set in a central aortic systolic pressure value set at a position corresponding to the position the arterial waveform being processed occupies in the arterial waveform dataset;

wherein a value of f corresponds with the $f^{th}$ blood pressure measurement, the functions of the interval means, averaging means, first storing means and second storing means steps (a)-(e) are repeated for each arterial waveform in the arterial waveform dataset and, for each such repetition, steps (c) and (d) are further repeated with the value of f commencing at 1 and being incremented by 1 each time until the value of f plus the integer interval value equals the predetermined number of blood pressure measurements in the set being processed.

5. The system of claim 1, wherein the predetermined number of blood pressure measurements for at least one arterial waveform in the dataset differs from the predetermined number of blood pressure measurements for the other arterial waveforms in the dataset.

6. The system of claim 1, wherein the set of blood pressure measurements substantially equates to a uniform distribution of values from the arterial waveform.

7. The system of claim 6, further comprising a means to determine the duration of the arterial waveform and where the predetermined number of blood pressure measurement is determined according to the following formula:

$$\text{Predetermined number} = sr \times t$$

where:
sr=the sample rate, in Hz, f a measuring device used to record the blood pressure measurements in the set; and t=the duration of the arterial waveform.

8. The system of claim 7, wherein the integer interval value is a division of the sample rate.

9. The system of claim 8, wherein the integer interval value is the sample rate divided by 4.

10. The system of claim 1, wherein the integer interval value is a division of the predetermined number.

11. The system of claim 10, wherein the integer interval value is within a range the boundaries of which are determined as follows:

$$i_{range} = n/(t \times v) \pm (n/(t \times 30))$$

where:
n is the predetermined number of blood pressure measurements in the set;

t is the duration of the waveform (in seconds); and v is a predetermined division value.

12. The system of claim 11, where v=4.

13. The system of claim 1, where the integer interval value is equal to 60 divided by a predetermined division value.

14. The system of claim 13, where the integer interval value is 15.

15. The system of claim 1, wherein the predetermined number of blood pressure measurements in the set is equal to or greater than 15.

16. The system of claim 15, wherein the predetermined number of blood pressure measurements in the set is at least 30.

* * * * *